(12) United States Patent
Moeller et al.

(10) Patent No.: US 8,486,085 B2
(45) Date of Patent: *Jul. 16, 2013

(54) SURGICAL MICROSCOPY SYSTEM AND METHOD FOR PERFORMING EYE SURGERY

(75) Inventors: Gerhard Moeller, Aalen (DE); Anja Seiwert, Aalen (DE); Michel Perez, Dijon (FR); Peter Amend, Vienna (AT)

(73) Assignee: Carl Zeiss Meditec AG, Jena (DE)

( * ) Notice: Subject to any disclaimer, the term of this patent is extended or adjusted under 35 U.S.C. 154(b) by 110 days.

This patent is subject to a terminal disclaimer.

(21) Appl. No.: 13/040,727

(22) Filed: Mar. 4, 2011

(65) Prior Publication Data

US 2011/0157553 A1    Jun. 30, 2011

Related U.S. Application Data

(62) Division of application No. 11/259,556, filed on Oct. 26, 2005, now Pat. No. 7,905,887.

(30) Foreign Application Priority Data

Oct. 26, 2004  (DE) .......................... 10 2004 052 031
Nov. 18, 2004  (DE) .......................... 10 2004 055 683

(51) Int. Cl.
    *A61F 9/00*    (2006.01)
(52) U.S. Cl.
    USPC ............................ 606/107; 351/211; 359/368
(58) Field of Classification Search
    USPC ................. 606/4–6, 107, 166; 351/208–211;
                                                    359/368–370, 385–389
    See application file for complete search history.

(56) References Cited

U.S. PATENT DOCUMENTS

| 6,010,497 | A  | * | 1/2000  | Tang et al. ........................ 606/5 |
| 6,159,205 | A  | * | 12/2000 | Herekar et al. ................. 606/17 |
| 6,607,527 | B1 |   | 8/2003  | Ruiz et al. |
| 7,846,152 | B2 | * | 12/2010 | Chernyak et al. ............... 606/10 |
| 7,905,887 | B2 | * | 3/2011  | Moeller et al. ................. 606/107 |
| 2002/0198516 | A1 |  | 12/2002 | Knopp et al. |
| 2003/0142271 | A1 |  | 7/2003  | Ross et al. |

(Continued)

FOREIGN PATENT DOCUMENTS

| DE | 69232640 T2 | 2/2003 |
| DE | 10226382 B4 | 1/2004 |

(Continued)

OTHER PUBLICATIONS

Rao, R., et al., "Innovative Digital Microsurgical Workstation Previewed at ASCRS", News Release, 3D Vision Systems, Inc., Apr. 15, 2004, pp. 1-2.

(Continued)

*Primary Examiner* — Ahmed Farah
(74) *Attorney, Agent, or Firm* — Potomac Patent Group, PLLC

(57) ABSTRACT

A surgical microscopy system comprises microscopy optics for generating an image of an eye under surgery. A pattern generator generates a pattern to be superimposed with the image. An eye-tracker is provided for tracking a position of the superimposed pattern with respect to the image in case of a movement of the eye. The superimposed pattern comprises pattern elements that are equally distributed on first and second circles of different sizes, in order to give assistance when placing a suture during a corneal transplant. The superimposed pattern may also provide an assistance for orientating a toric intra-ocular lens.

12 Claims, 4 Drawing Sheets

U.S. PATENT DOCUMENTS

2004/0102799 A1 5/2004 Perez et al.
2005/0284864 A1 12/2005 Yamada
2006/0100677 A1* 5/2006 Blumenkranz et al. ......... 607/89

FOREIGN PATENT DOCUMENTS

| JP | 08280624 A | 10/1996 |
| JP | 2004081830 A | 3/2004 |
| JP | 2004073892 A | 11/2004 |
| JP | 2005-308385 | 11/2005 |
| WO | 9308877 A1 | 5/1993 |

OTHER PUBLICATIONS

Rao, R., "Digital Microsurgical Workstation Reveals 3-D Image of Eye", Ophthalmology Times Meeting E-News, May 1, 2004, p. 1.
English translation of Japanese Office Action dated Dec. 8, 2011 in corresponding Japanese Application No. 2005-309581.
English Translation of Notification of Reasons for Rejection issued in corresponding Japanese Patent Application No. 2011-114682, dated Jan. 10, 2013.

* cited by examiner

SURGICAL MICROSCOPY SYSTEM AND METHOD FOR PERFORMING EYE SURGERY

This application is a Divisional of co-pending application Ser. No. 11/259,556, filed on Oct. 26, 2005, which claims priority to Application No. 10 2004 052 031.3 filed in Germany on Oct. 26, 2004, and Application No. 10 2004 055 683.0 filed in Germany on Nov. 18, 2004, the entire contents of which are hereby incorporated by reference into the present application and for which priority is claimed under 35 U.S.C. §120.

BACKGROUND OF THE INVENTION

1. Field of the Invention

The present invention relates to a surgical microscopy system for performing eye surgery. The invention also relates to a method of performing a surgery on the eye. Further, the invention relates to a method of preparing a surgery on the eye.

2. Brief Description of Related Art

An example of an eye surgery is a corneal transplantation. In such surgery, an original cornea is removed within a circular region, and a corresponding circular graft is inserted to replace the removed cornea. The inserted graft is sewn to the remaining natural cornea. A corresponding suture should be set with regular stitches, in order to not disturb a symmetry of the eye. In particular for a relatively inexperienced surgeon it is difficult to place the stitches of the suture with a sufficient regularity.

Another example of an eye surgery is a cataract surgery. In a cataract surgery, the natural lens of the human eye, in which a cataract has developed, is replaced by an artificial lens. The surgery is a micro-surgical treatment performed by an operating surgeon using a surgical microscope. An opening in the lens capsule is achieved within the inner rim of the iris by providing an incision through the sclera or cornea without injuring the iris. The body's natural lens is removed via this incision by breaking the natural lens into pieces using ultrasonic energy and removing the pieces using a suction device. The artificial lens is then inserted into the lens capsule through the opening.

US 2004/0102799 A1 discloses a surgical microscopy system projecting a ring pattern into a microscopic image of the eye to be operated upon. The projected ring pattern helps the operating surgeon to place a correct incision into the lens capsule. The operating surgeon can use the projected ring pattern as a guide for performing the cut. Thereby it is possible to precisely adjust a diameter of the incision relative a diameter of the artificial lens that is to be inserted. This reduces adverse long-term consequences of the treatment. Using the surgical microscopy system projecting the ring pattern, long-term consequences are somewhat reduced as compared to the conventional treatment in which the operating surgeon places the incision merely by visual judgment. Despite improvements in the conventional eye-surgery microscopy system, expectations are still high regarding reduction of long-term consequences and further improvements appear to be possible.

SUMMARY OF THE INVENTION

The present invention has been accomplished taking the above problems into consideration.

Embodiments of the present invention provide a surgical microscopy system and method for performing a surgery on an eye of a patient.

According to an embodiment of the invention, an eye surgery microscopy system comprises microscopy optics for generating an image of an eye arranged in one object plane of the microscopy optics, and a pattern generator for the generation of a pattern to be superimposed on the image.

The pattern can be for example a circle pattern that can serve as a guiding line for the operating surgeon for placing an incision in the lens capsule of the operated eye. However, the pattern can also be a pattern, other than a circle pattern that can assist the operating surgeon in another respect.

According to an embodiment of the present invention, the surgical microscopy system comprises an eye-tracker in order to detect a position of the operated eye in the image, and to adapt a position of the superimposed pattern relative to the image in dependence of the detected position of the eye in the image. In particular, the position of the pattern in the image can be fixedly maintained relative to the image of the eye.

It has been observed that a force exerted by a surgical tool, such as a scalpel or a shear, may shift an eyeball within an eye socket of the patient relative to the microscopy optics in an unforeseeable way, and thus relative to the object plane of the microscopy optics. In this case, if a cut is produced along a guiding line of a statically superimposed ring pattern, the cut may have a shape that does not correspond to a desired shape.

By using the eye-tracker that produces a position signal in dependence of the detected position of the eye, and by configuring the pattern generator such that the pattern generator changes the position of the pattern in the image in dependence of the position signal, it is possible to achieve a more precise cuts and other manipulations on the eye under surgery. Still, the representation of the eye will continuously be displaced within the image due to the application of forces exerted by the surgical tools. However, due to the function of the eye-tracker in combination with the pattern generator, the superimposed pattern will be displaced in correspondence with the displacements of the image of the eye, and the surgeon can achieve a better success by tolerating the permanent displacements of the pattern relative to the image.

According to an exemplary embodiment of the invention, the eye-tracker comprises an image processor that configured to detect a center of a contiguous dark region in the image and to provide the position signal in such that it represents the center of the dark region. In this respect, it may be of advantage to illuminate the operated eye such that an inside of the pupil appears as a dark region. In such treatments, an inner rim of the pupil is usually clearly defined and is maintained in a substantially constant position relative to a center of the eye. Thus, the centre of the eye is typically well detectable by the above image processor even during difficult operation conditions.

According to a further embodiment of the present invention, a surgical microscopy system comprises a microscopy optics for generating an image of an object plane and a pattern generator for generating a pattern superimposed with the image. The pattern generator generates the superimposed pattern such that the pattern comprises two groups of pattern elements. Each group of pattern elements comprises plural pattern elements. The pattern elements of the first group are distributed on a first circle, and the pattern elements of the second group are distributed on a second circle. The second circle is completely arranged within the first circle. In this respect, said first and the second circles can have a substantially common centre. In the context of the present application, the centers of the first and second circles are substantially the same if a between the centre of the first circle and the centre of the second circle is smaller than 0.15 times, and in particular smaller than 0.07 times a diameter of the second circle.

When performing an implantation of a cornea, the operating surgeon can use the superimposed pattern elements as reference points in order to provide stitches for a suture for holding the implant at locations where the pattern elements appear in the image. Thus, when placing the suture, the operating surgeon no longer has to rely on his estimation by sight that is free and subject to deceptions. Rather, a desired stitching pattern can be entered into the pattern generator via an interface before the execution of the treatment as data representing the stitch pattern. This is performed in a way such that the pattern generator displays the pattern elements, which can be used by the operating surgeon as auxiliary markings, at the respective positions in the microscopic image.

The interface may comprise a first interface portion for inputting diameters of the first and second circles. Furthermore, the interface may comprise a second interface portion for inputting a number of the pattern elements of the first group or the number of the pattern elements of the second group. Further, the interface may comprise a third interface portion for inputting a circumferential position of the pattern elements of the first group relative to a circumferential position of the pattern elements of the second group. In this way different suture types, such as a zigzag type suture and a suture that comprises a multiplicity of stitches extending in a radial direction, can be easily predefined.

According to an exemplary embodiment, the diameters of the first and second circles differ by a ratio from 0.5 to 0.8. According to a further exemplary embodiment, a dimension of the pattern elements in the image is large enough to be easily noticed by an operating surgeon, but at the same time small enough to define the place of the stitch that is to be performed with a sufficient precision.

The pattern elements can exhibit an arbitrary compact shape, such as a shape of a circle, a filled circle, a rhombus or similar shapes. Further the pattern elements my also be represented by shapes such as crosses, stars and similar shapes.

According to a further embodiment of the invention, a method of preparing of a surgical treatment of the eye comprises: generating a microscopic image using a microscopy optics such that at least a portion of an iris or a portion of a limbus of the eye under surgery is visible in the image, and generating a pattern superimposed with the microscopic image, wherein the pattern comprises a first group of plural pattern elements disposed on a first circle, and a second group of plural pattern elements disposed on a second circle which is located within an interior of the first circle.

According to a further embodiment of the invention, a surgical microscopy system comprises a microscopy optics for generating an image of an object plane of the microscopy optics, and a pattern generator for generating of a pattern to be superimposed with the image.

The pattern generator is configured to generate a first partial pattern essentially extending along a ring, and a second partial pattern essentially extending along a straight line, wherein the straight line has two intersections with the ring, and wherein an orientation of the straight line is changeable around a centre of the ring. According to an exemplary embodiment, the pattern comprises a TABO-pattern displaying an angular scale. The TABO-pattern is well known to the person skilled in the art as a pattern allowing measurement of angles at the eye.

Such type of pattern is particularly helpful with regard to inserting of toric intraocular lenses (IOL) into an eye of a patient. When performing a conventional method, the operating surgeon was dependent on his free estimation by sight. Therefore, it has been difficult to ensure a desired orientation of the toric intraocular lens relative to the eye. Since the partial pattern extending along the straight line is superimposed with the microscopic image by using the pattern generator, it possible for the operating surgeon to use this partial pattern as an assistance in orientating the intraocular lens. In this respect the intraocular lens itself can exhibit markings or design characteristics. The operating surgeon can shift the intraocular lens relative to the recognized image such that the markings and/or design characteristics provided on the intraocular lens coincide or are registered with the partial pattern extending along the straight line. The partial pattern extending along the ring can be useful in order to correctly position the partial pattern extending along the straight line relative to the image. This can be achieved by shifting the microscopy optics relative to the eye. It is, however, also possible to input positioning signals to the pattern generator via an interface, to instruct the pattern generator to shift the generated pattern in the image as a whole according to the entered signals. When using the eye-tracker it may be possible to not generate the first partial pattern extending along the ring during time intervals, to not generate the first partial pattern at all.

According to a further exemplary embodiment, the surgical microscopy system comprises an interface for inputting an orientation and/or a change of the orientation of the straight line in the image.

In accordance with a further embodiment of the invention, a method of preparing an implantation of a toric intra-ocular lens comprises: generating a microscopic image, using a microscopy optics, such that at least a portion of an iris or a portion of a limbus of an eye to be operated upon is visible in the image, superimposing onto the image a second partial pattern essentially extending along a straight line, and adjusting an orientation of the second partial pattern.

According to an embodiment, the orienting of the straight line is performed by firstly changing the orientation of the straight such that the mark coincides with a mark applied to the operated eye, wherein such mark has been applied to the eye before starting the treatment of the eye. Such mark may represent a predetermined orientation, such as a vertical orientation. Since the eye can be shifted and also rotated in the eye socket during the treatment, this mark applied to the eye constitutes a reference for an orientation of the toric intraocular lens. After the straight line has been oriented such that it coincides with the mark applied to the eye, the orientation of the straight line is then changed by a predetermined angular amount that corresponds to a desired orientation of the intraocular lens with respect to the eye.

BRIEF DESCRIPTION OF THE DRAWINGS

The foregoing as well as other advantageous features of the invention will be more apparent from the following detailed description of exemplary embodiments of the invention with reference to the accompanying drawings. It is noted that not all possible embodiments of the present invention necessarily exhibit each and every, or any, of the advantages identified herein.

DETAILED DESCRIPTION OF EXEMPLARY EMBODIMENTS

Figure 1:
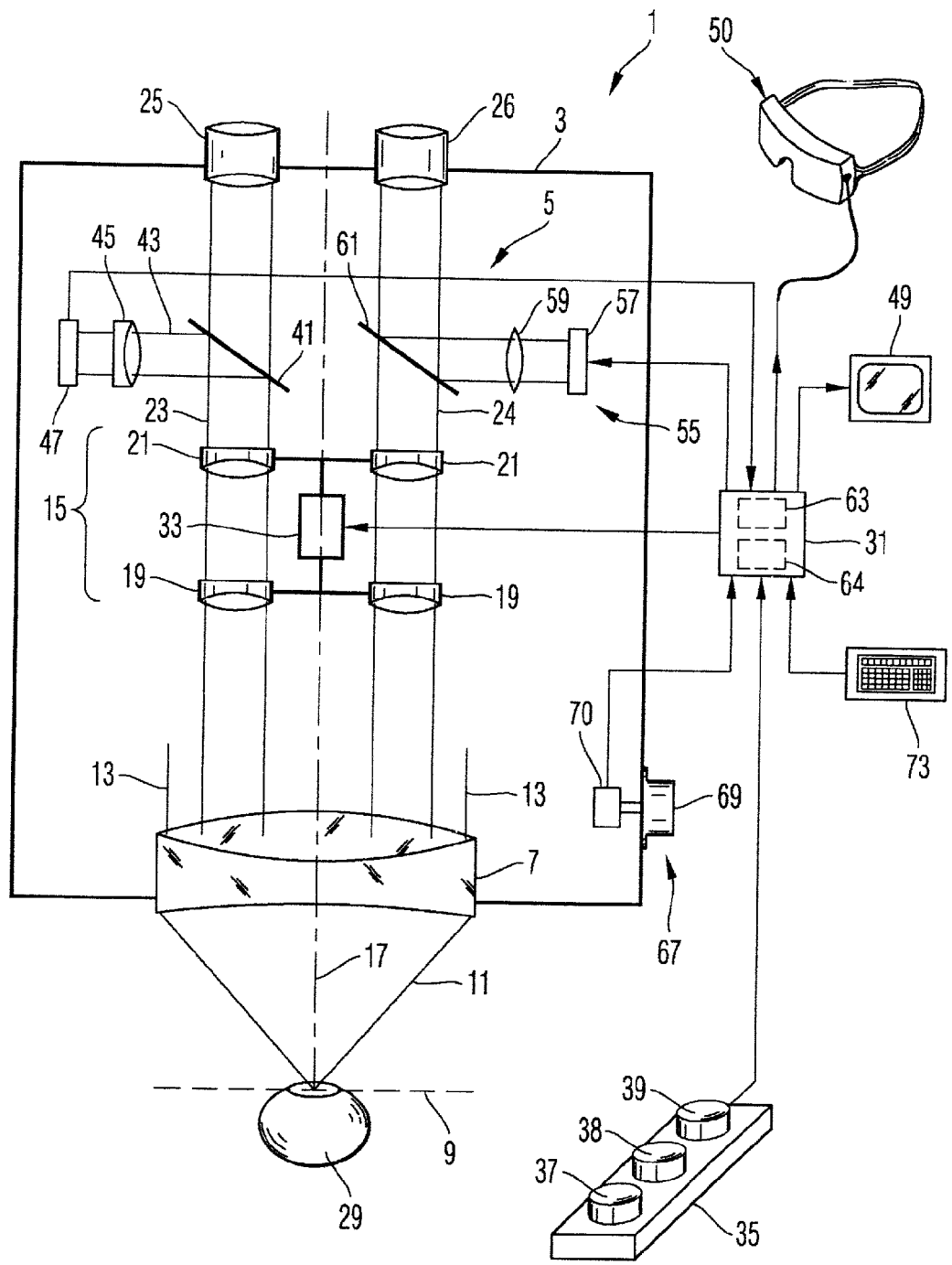
FIG. 1 is a schematic illustration of a surgical microscopy system according to an embodiment of the present invention.

In the exemplary embodiments described below, components that are alike in function and structure are designated as far as possible by alike reference numerals. Therefore, to understand the features of the individual components of a specific embodiment, the descriptions of other embodiments and of the summary of the invention should be referred to.

FIG. 1 schematically illustrates a surgical microscopy system 1. The surgical microscopy system 1 comprises a housing body 3 for mounting microscopy optics 5. The microscopy optics 5 comprises an objective lens 7 transforming an object-side divergent beam 11 emanating from an object plane 9 of the objective lens 7 into an image-side parallel beam 13. A pair of zoom systems 15, each comprising groups 19 and 21 of lenses which are displaceable in a direction of an optical axis 17 of the objective lens 7, supply two partial beams 23 and 24 of the image-side parallel beam 13 to oculars 25 and 26. The operating surgeon can look with his left and right eyes into the oculars 25, 26 in order to perceive an image of the object plane 9.

For performing an eye surgery, the operating surgeon arranges the microscopy system 1 in front of an eye 29 of a patient. For performing a cataract surgery, the operating surgeon first creates an entrance to a lens capsule of the eye, for example by accomplishing appropriate incisions at a sclera or a cornea of the eye 29. Then, preparatory steps for providing an incision at the lens capsule are performed. For this purpose, the microscopy system 1 comprises a controller 31, such as a personal computer, that controls a motor 33 for displacing the groups of lenses 19, 21 of the zoom systems 15 and, thus, for changing a magnification of the microscopy optics 5. The controller 31 receives commands for controlling the motor 33 from a switch desk 35 having push-buttons 37, 38 and 39 that are operable by a foot of the operating surgeon or a person preparing the incision at the lens capsule. If the push-button 37 is pressed, the controller 31 controls the motor 33 such that the magnification of the microscopy optics 35 is increased. Similarly, when pressing the push-button 38, the magnification of the microscopy optics is decreased.

The microscopy system 1 further comprises a semi-permeable mirror 41 disposed in the beam 23 for supplying a portion 43 of the beam 23 to a camera chip 47 via an adapting optics 45 such that an image of the object plane 9 is generated on the camera chip 47. The controller 31 reads out images detected by the camera chip 47 and displays the images on a display 49. Thus the same image of the object plane 9 as it is perceived by a viewer looking into the ocular 25 is visible on the display 49.

This image further displayed on a head mounted display 50 that can be carried by a person, such as the operating surgeon, on his head. Thus, operating surgeon has three different possibilities of watching the object plane. A first possibility of looking into the oculars, a second possibility of watching the operation field on the display 49 and a third possibility of watching the operation field by using the head mounted display 50. In the case of using the head mounted display 50 it is advantageous to provide a camera system as it is represented in FIG. 1 by the components 41, 43, 45 and 47 for the left beam path in both stereoscopic optical beam paths of the microscopy system 1. Thus, the two cameras can generate a stereoscopic image of the object plane 9, and this image can be displayed in a stereoscopic way by the head mounted display 50.

Figure 2:
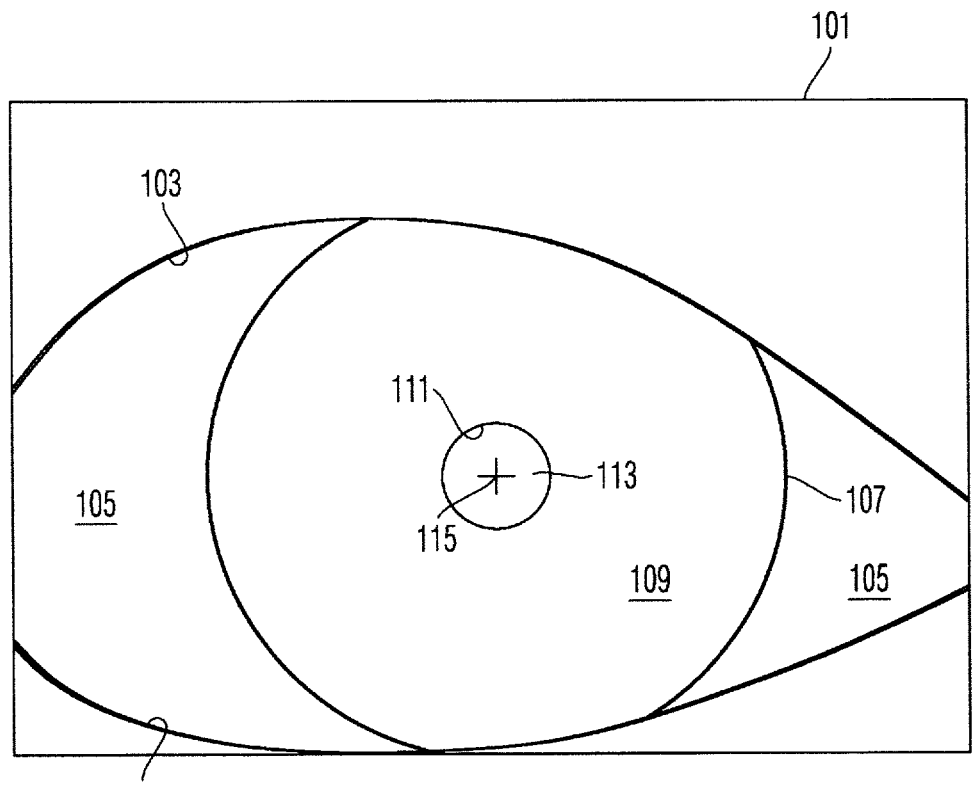
FIG. 2 is a schematic representation of an image generated by the microscopy system of FIG. 1.

The controller 31 is part of an eye-tracker. For implementing the eye-tracker, the controller 31 comprises a software module 63 for analyzing the images received from the camera 47. A representative illustration of such image 101 is shown in FIG. 2. Lids 103, a sclera 105, an outer rim 107 of a pupil 109 and an inner rim 111 of the pupil 109 can be recognized in the image 101. By using an appropriate illumination of the eye, the sclera 105 appears as a white area, the iris 109 appears as an area having a colour corresponding to the eye colour of the patient, and the pupil 113 positioned within the inner rim 111 of the iris 109 appears as a dark or black area. The software module 63 analyzes the image with respect to its brightness values and provides a threshold filter with regard to brightness. By applying the filter, only those regions of the image, which have a brightness below a threshold value, are maintained in the image.

This typically results in a contiguous dark region 113 of the pupil and further smaller details of the image 101, such as lashes or similar. Thereafter, the image processing software determines a largest contiguous dark region which will correspond to the pupil 113 in practice. A geometrical centre of gravity of the largest contiguous dark region is determined. The reference sign 115 in FIG. 2 designates such geometrical center of gravity. Thus it is possible to determine the center 115 of the pupil in the coordinates of the image 101 by using the eye-tracker.

The microscopy system 1 further comprises a projector 55 having a display 57, such as a LCD display, projection optics 59 and a semi-permeable mirror 61. The semi-permeable mirror 61 is arranged in the beam 24 and superimposes a projected pattern displayed by the display 57 and optics 59 with the beam 24 such that it is perceived in superposition with the image of the object plane 9 when looking into the ocular 26 or the head mounted display 50 or when looking on the display 49. The pattern displayed by the display 57 is generated by a pattern generator 64 that is part of the controller 31, wherein the controller 31 further superimposes this pattern onto the image that is shown on the display 49. In this respect, the controller generated the pattern superimposed with the image in a size that automatically scales with the adjusted magnification of the zoom systems 15. Thus, if the user changes the magnification of the zoom system 15 by a certain factor, the controller 31 also changes the size of the superimposed pattern by the same factor.

Figure 3:
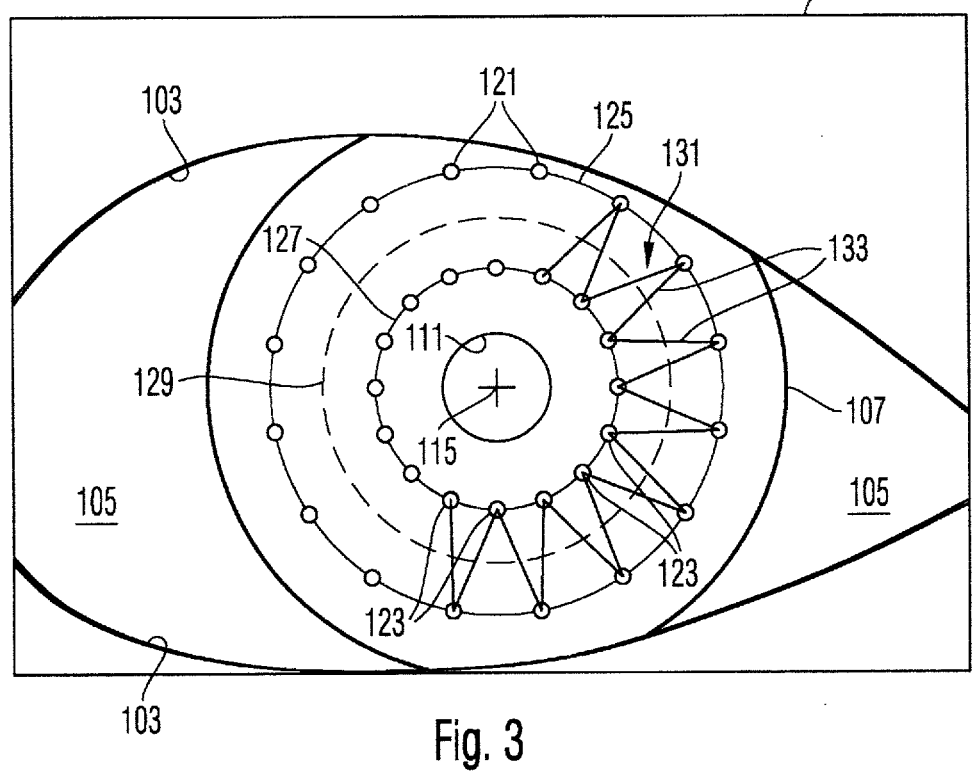
FIG. 3 is a schematic representation of an image corresponding to the image of FIG. 2, wherein a marker pattern for assisting in setting a suture during a corneal transplantation is superimposed with the image.

FIG. 3 shows the microscopic image 101 of the object plane (compare with FIG. 2), wherein a pattern generated by the pattern generator 64 is superimposed with the image. The pattern comprises of a plurality of small rings 121 as outer pattern elements and a plurality of small rings 123 as inner pattern elements. The small rings 121 are located on a circle 125. The circle 125 does not necessarily have to be displayed in the image 101. The small rings 123 are located on a further circle 127 that is located within the circle 125. It is also not necessary that the circle 127 is displayed in the image 101. Broken line 129 designates a border between a natural cornea of the eye that is located outside of the circle 129, and a cornea implant, that is located in an interior of the circle 129. A zigzag type suture 131 fixes the implant to the cornea. Straight sections 133 of a thread providing the suture extend between the rings 121 and 123. The rings 121 and 123 that are superimposed in the image 101 serve the operating surgeon as positioning aids for stitches fixing the thread 133. In the described example, the suture comprises thirty-two stitches corresponding to sixteen rings 121 which are equally distributed on the outer circle 125, and sixteen rings 123 which are equally distributed on the inner circle 127. In the illustrated example, a diameter of the circle 127 is about 0.7 times a diameter of the circle 125.

The number of the rings 121, 123 and the diameters of the circles 125 and 127 are adapted to the circumstances and conditions of the transplantation to be accomplished and can be input by using the keyboard 73 of the controller 31.

Figure 4:
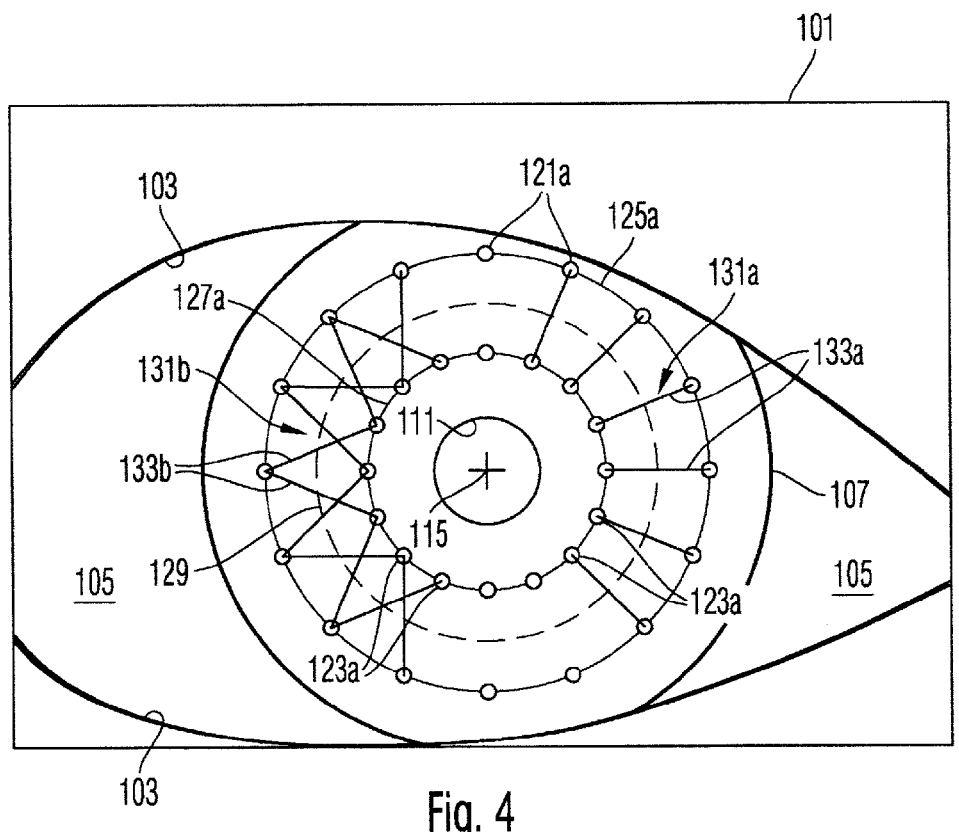
FIG. 4 is a schematic representation of an image corresponding to the image of FIG. 2, wherein a marker pattern for assisting in setting a suture during a corneal transplantation is superimposed with the image.

FIG. 4 shows a superimposed pattern comprising rings 121 as pattern elements arranged on an outer circle 125 and rings 123 as pattern elements arranged on an inner circle 127. The rings 121 and 123 are not shifted relative to each other in circumferential direction. Thus, pairs of rings 121, 123 are aligned in a radial direction relative the center 115 of the pupil. This pattern of the rings 121, 123 can be used for producing a radial suture 131*a*, as this is shown on the right side of FIG. 4. In this case, pieces 113*a* of a thread are inserted in-between radially aligned pairs of rings 121, 123. Furthermore, the pattern 121, 123 can be used for the provision of a double zigzag suture 131*b*, as this is shown on the left side of FIG. 4 by thread portions 133*b*.

The eye-tracker is 63 constantly active during the surgery. Thus, the superimposed pattern 121, 127 is moved along with the microscopic image of the eye, if the eye is displaced relative to the microscopy optics 5 due to a force on the eye exerted by a surgical tool.

A method of introducing a toric intra-ocular lens 131 into a lens capsule of an eye will now be described with reference to FIGS. 5 to 7. Due to its astigmatic optical effect, the toric intraocular lens 131 has to be correctly oriented about a centre 115 of a pupil 113. During the treatment, the pupil is dilated due to administration of a suitable drug. In consequence, a distance between an inner rim 111 and an outer rim 107 of an iris is reduced in FIG. 7 as compared to the illustrations of FIGS. 2 to 4.

The intra-ocular lens 131 comprises a central lens portion 133 and opposite extended peripheral portions each including a haptics 135. The haptics 135 are characteristic features of the intra-ocular lens which serve as marks and can be clearly recognized in the microscopic image. However, it is also possible that additional marks, such as lines, are provided on the lens 131 in order to be used as orientation aids. In the illustration shown in FIG. 7, a mark produced by the pattern generator 64 is superimposed with the microscopic image 101. The mark comprises a circular line 141 and a straight line 143. A diameter of the circular line 141 can be input via the keyboard by the operating surgeon or an assisting person preparing the surgery. In the situation shown in FIG. 7 the diameter is selected such that it is between a diameter of the inner rim 111 and a diameter of the outer rim 107 of the iris. An orientation of the straight lines 143 about a center of the circular line 141, which coincides with the centre 115 of the pupil in a situation of a correct positioning of the circular line 141, is selected such that it provides an optimal orientation of the intraocular lens 131. Thus, by using the straight line 143, the operating surgeon can orient and position the intra-ocular lens 131 in the correct desired orientation relative to the eye.

Figure 6:
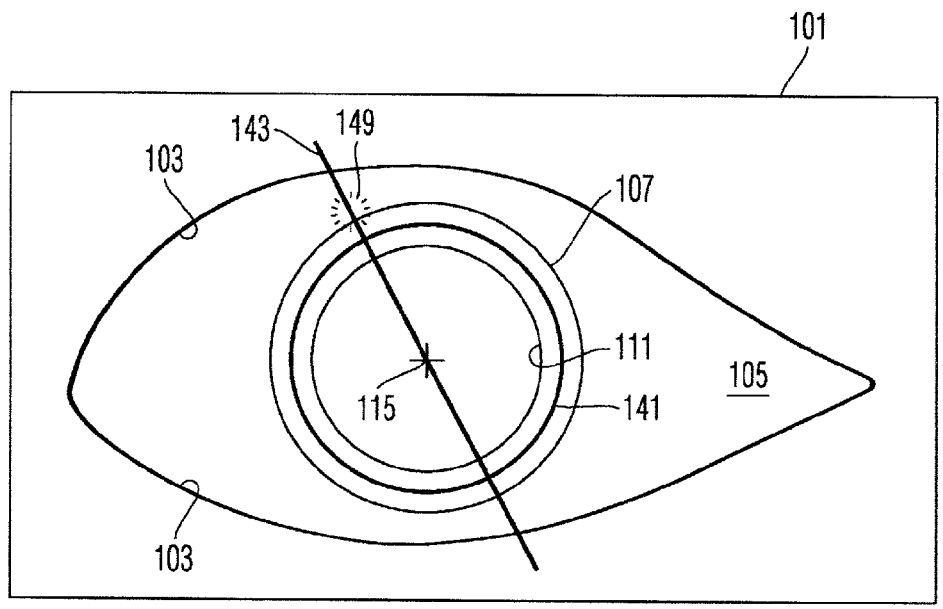
FIG. 6 is a schematic representation of an image generated by the microscopy system corresponding to the representation of FIG. 5, wherein an auxiliary pattern is displayed for orienting the intraocular lens in an intermediate step.
Figure 7:
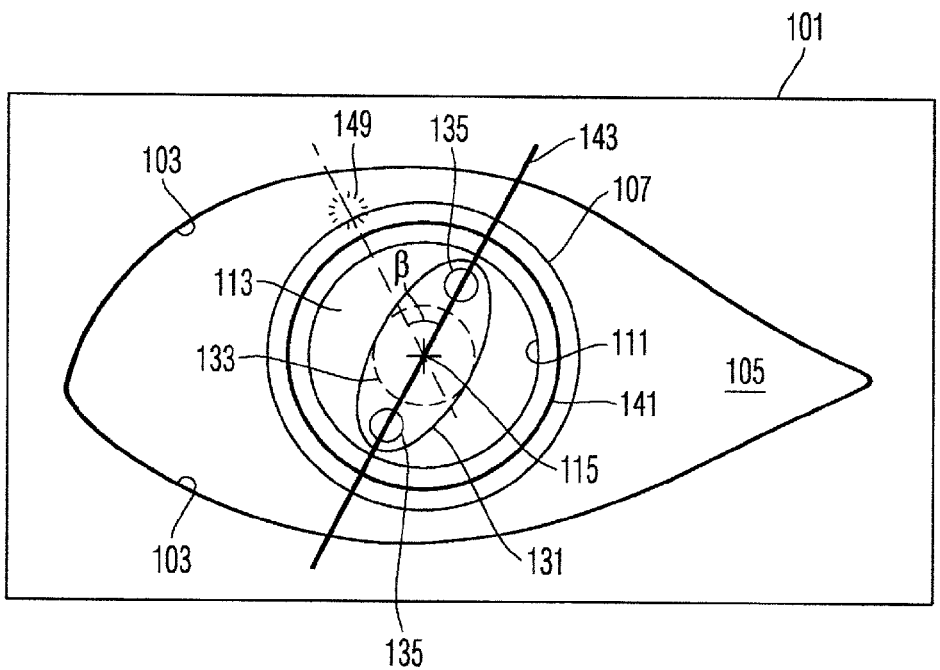
FIG. 7 is a schematic representation of an image generated by the microscopy system corresponding to the representation of FIG. 5, wherein the auxiliary pattern is displayed for orienting the intraocular lens in a further intermediate step.

The correct orientation of the straight line 143 that is shown in FIG. 7 is adjusted as follows: FIG. 5 shows the eye before the introduction of the intra-ocular lens. Before the treatment, a mark 149 has been attached to the eyeball by using a suitable tool, such as color pen or other instrument. The mark 149 is oriented in accordance with a predetermined angle α with respect to a vertical reference 151 or a horizontal reference which has been marked before the treatment. In a step that is shown in FIG. 6 the circular line 141 and the straight line 143 generated by the pattern generator 64 are superimposed with the microscopic image. The operating surgeon or assisting person preparing the surgery orients the straight line 143 such that the straight line 143 is registered with the mark 149 attached to the eye. Then a signal is input to the pattern generator 124 to change the orientation of the straight line 143 by an angle β such that the straight line has the orientation shown in FIG. 7. This orientation defines the correct orientation of the intraocular lens 131. Thus, it is possible to insert the intraocular lens in an orientation that has been determined before the treatment relative to the marking 149. An accuracy of the insertion does not depend on the orientation which the eye actually has in the image 101 during the operation. The reason is that it is difficult to define the orientation of the eye in the image 101, since firstly the orientation of the microscopy optics 5 relative to the head of the patient is not well defined and secondly the orientation of the eye in the eye socket can change during the treatment.

In the embodiments illustrated with reference to FIGS. 3 and 4 the pattern elements are small circles. It is however possible to represent these pattern elements in another way such as for example by squares, lozenges, crosses, stars and similar patterns.

Figure 5:
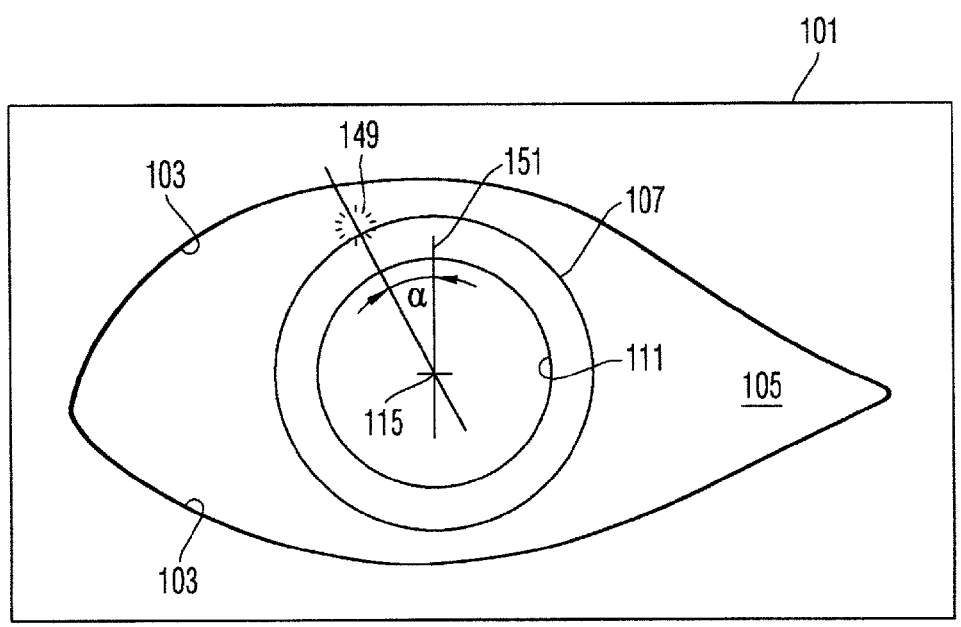
FIG. 5 is a schematic representation of an image generated by the microscopy system of FIG. 1 before insertion of an intra-ocular lens.

In the embodiment illustrated with respect to FIGS. 5 to 7, the orientation aid for the positioning of the intraocular lens is a continuous straight line. It is, however, also possible to use other types of marking for orientating the intraocular lens, provided that an orientation of such marking about a center of the pupil can be adjusted with a sufficient accuracy. For example, this marking may comprise plural portions of a straight line or portions of plural straight lines crossing each other, wherein plural of such portions may be registered with suitable characteristic features of the intraocular lens by correctly orienting the intraocular lens relative to the eye.

Furthermore, with the embodiment illustrated with reference to FIGS. 5 and 6, it is possible to omit the inserted circle 141 as a partial pattern if it is to a sufficient extent ensured that the straight line 143 extends through the centre 115 of the pupil. This can be achieved in particular if the position of the inserted pattern is adjusted relative to the image of the eye by using the eye-tracker illustrated above.

It is further possible to superimpose a pattern referred to as a TABO pattern in the art with the image, rather than merely superimposing the straight line and circle pattern with the image. The TABO pattern exhibits a plurality of single marks that are arranged relative to one another at the same angular distances about a center of the pattern. The marks of the TABO pattern can be used as the orientational aid.

Apart from orienting an intraocular lens, the superimposed patterns can also be used for other purposes where it is important to maintain a desired orientation relative to the eye. An example of such surgery is a placement of a limbal relaxing incision (LRI).

Advantageously, the eye-tracker can also be used for placing a circular incision into the lens capsule before removing the natural lens. For such purpose, the pattern generator may generate a circular pattern as illustrated, for example, in US 2004/0102799 A1. The entire contents of this document are incorporated herein by reference.

In the above described embodiments the position signal of the eye-tracker is used to compensate movements of the eye. This is performed by adjusting the position of the pattern superimposed with the image relative to the image in dependence of the position signal. Alternatively or in addition thereto, it is also possible to displace the microscopy optics relative to the eye under surgery and in dependence of the position signal of the eye-tracker. For this purpose, the microscopy optics can be supported by a stand and positioned relative to the eye. The stand may comprise an actuator for adjusting a position of the microscopy optics relative to the eye, wherein the actuator is controlled in dependency of the position signal of the eye-tracker in order to generate the image of the eye arranged in the object plane such that it appears in an substantially fixed position within the image.

While the invention has been described with respect to certain exemplary embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

What is claimed is:

1. A surgical microscopy system for performing a surgery on an eye, wherein the system comprises:
    a microscopy optics for generating an image of an object plane of the microscopy optics;
    a pattern generator for generating a pattern superimposed with the image; and
    an eye-tracker for detecting a position of the eye relative to the image and to generate a position signal indicative of the detected position;
    wherein the pattern generator is configured to change a position of the pattern in the image responsive to the position signal.

2. The surgical microscopy system according to claim 1, wherein the eye-tracker comprises an image processor which is configured to determine a center of a contiguous dark region in the image and to generate the position signal based on a position of the determined center of a contiguous dark region.

3. The surgical microscopy system according to claim 2, wherein the image processor comprises a threshold filter applied to pixels of the image, such that pixels having a brightness value below a threshold are set to a first value and pixels having a brightness above the threshold are set to a second value.

4. The surgical microscopy system according to claim 1, further comprising a sixth interface for inputting a size of the generated pattern relative to the image.

5. The surgical microscopy system according to claim 1, wherein a magnification of the microscopy optics is adjustable, and wherein the pattern generator is configured to generate the pattern such that a size of the pattern is proportional to the magnification of the microscopy optics.

6. The surgical microscopy system according to claim 1, wherein the pattern comprises a ring pattern.

7. The surgical microscopy system according to claim 1, wherein the pattern generator comprises a projector for superimposing the pattern with a beam path of the microscopy optics.

8. The surgical microscopy system according to claim 7, wherein the projector is configured to project the pattern in a direction towards an ocular of the microscopy optics.

9. The surgical microscopy system according to claim 7, wherein the projector is configured to project the pattern in a direction towards the object plane.

10. The surgical microscopy system according to claim 1, further comprising a screen for displaying the image generated by the microscopy optics and the pattern generated by the pattern generator and superimposed with the image.

11. The surgical microscopy system according to claim 1, further comprising a head mounted display for displaying the image generated by the microscopy optics and the pattern generated by the pattern generator and superimposed with the image.

12. The surgical microscopy system according to claim 1, further comprising an ocular for displaying the image generated by the microscopy optics and the pattern generated by the pattern generator and superimposed with the image.

* * * * *